United States Patent [19]
Brugger

[11] Patent Number: 5,948,251
[45] Date of Patent: Sep. 7, 1999

[54] TECHNIQUE FOR USING A DIALYSIS MACHINE TO DISINFECT A BLOOD TUBING SET

[75] Inventor: James Brugger, Boulder, Colo.

[73] Assignee: COBE Laboratories, Inc., Lakewood, Colo.

[21] Appl. No.: 08/966,007

[22] Filed: Nov. 7, 1997

Related U.S. Application Data

[62] Division of application No. 08/481,754, Jun. 7, 1995, Pat. No. 5,685,835.

[51] Int. Cl.$^6$ .............................. A61L 2/00; B01D 36/00; B01D 65/00
[52] U.S. Cl. .................... 210/252; 210/175; 210/251; 210/258; 210/321.69; 210/636; 210/646; 422/1; 422/28
[58] Field of Search ................................. 210/636, 646, 210/321.6, 251, 321.69, 252, 258, 175; 422/1, 28; 134/22.1, 22.11, 22.12, 37

[56] References Cited

U.S. PATENT DOCUMENTS

| | | | |
|---|---|---|---|
| 4,166,031 | 8/1979 | Hardy | 210/96.2 |
| 4,695,385 | 9/1987 | Boag | 210/636 |
| 4,770,787 | 9/1988 | Heath et al. | 210/646 |
| 5,183,569 | 2/1993 | Kyriacou | 210/636 |
| 5,259,961 | 11/1993 | Eigendorf | 210/646 |
| 5,268,144 | 12/1993 | Heilmann et al. | 422/26 |
| 5,409,612 | 4/1995 | Maltais et al. | 210/636 |
| 5,484,397 | 1/1996 | Twardowski | 604/5 |
| 5,591,344 | 1/1997 | Kenley et al. | 210/636 |
| 5,772,624 | 6/1998 | Utterberg et al. | 604/4 |

FOREIGN PATENT DOCUMENTS 2700121  7/1994  France.

*Primary Examiner*—John Kim
*Attorney, Agent, or Firm*—John R. Ley

[57] ABSTRACT

A method of disinfecting a blood tubing set on a dialysis machine after the blood tubing set has been used in a dialysis treatment. One end of the blood tubing set is connected to a disinfection port on the dialysis machine and an opposite end of the blood tubing set is connected to a waste drain. The dialysis machine provides a supply of a disinfectant solution to the disinfection port. A blood pump on the dialysis machine pumps the disinfectant solution from the disinfection port to the waste drain through the blood tubing set to expel contaminants from the blood tubing set. The blood tubing set is preferably connected to a dialyzer which is disinfected when the disinfectant solution is pumped through the blood tubing set. A supply of cleaning solution or water may be pumped through the blood tubing set and dialyzer to expel the disinfectant solution. A supply of air may be pumped through the blood tubing set and dialyzer to expel substantially all fluid from the blood tubing set and dialyzer. A dialysis machine includes hydraulic components for mixing and heating the disinfectant and cleaning solutions and for supplying the disinfectant solution, the cleaning solution, water and air to the disinfection port.

21 Claims, 7 Drawing Sheets

TECHNIQUE FOR USING A DIALYSIS MACHINE TO DISINFECT A BLOOD TUBING SET

This is a divisional of application Ser. No. 08/481,754, filed Jun. 7, 1995, issused as U.S. Pat. No. 5,685,835, on Nov. 11, 1997.

The present invention relates to a new and improved dialysis machine and technique for cleaning and disinfecting a disposable blood tubing set which connects a patient to the machine.

CROSS REFERENCE TO RELATED INVENTIONS

This invention is related to the inventions described in U.S. patent applications for Technique for Automatically Preparing a Dialysis Machine at a Predetermined Date and Time, Ser. No. 08/484,013, now U.S. Statutory Invention Registration No. H1658, published Jul. 1, 1997; and Technique for Priming and Recirculating Fluid Through a Dialysis Machine to Prepare the Machine for Use, Ser. No. 08/481,755, now U.S. Pat. No. 5,650,071, issused Jul. 22, 1997, both of which were filed concurrently therewith. Both of these applications are further assigned to the assignee hereof. The disclosures of these applications are further incorporated herein by this reference.

BACKGROUND OF THE INVENTION

A dialysis system is used as a substitute for the natural kidney functions of a human body. The dialysis system cleans the blood of the natural accumulation of bodily wastes by separating the wastes from the blood outside or extracorporeally of the body. The separated wastes are discharged and the cleansed blood is returned to the body.

The dialysis system consists of a dialysis machine, a dialyzer, a disposable blood tubing set and a supply of chemicals for producing a dialysate solution used within the dialyzer. The dialyzer is used with the dialysis machine to separate the wastes from the blood. The dialyzer includes a porous membrane located within a closed housing which effectively separates the housing into a blood compartment and a dialysate or filtrate compartment. The blood removed from the patient flows through the disposable blood tubing set and the blood side of the dialyzer. The dialysate solution prepared from the chemicals is passed through the dialysate side of the dialyzer. The wastes from the blood pass through the membrane by osmosis, ionic transfer or fluid transport into the dialysate and, depending upon the type of dialysis treatment, desirable components from the dialysate may pass in the opposite direction through the membrane and into the blood. The transfer of the wastes into the dialysate cleanses the blood while allowing the desired components from the dialysate to enter the bloodstream.

The transfer of blood between the patient and the dialyzer occurs within a disposable blood tubing set. The blood tubing set and the dialyzer represent a closed extracorporeal path through which the patient's blood travels. The blood tubing set includes an arterial line connected to an arterial reservoir for drawing blood from a patient, a venous line connected to a venous reservoir for returning blood to the patient, and a number of other lines for connecting a pump and the dialyzer between the arterial and venous reservoirs. Before the blood tubing set and the dialyzer can be used in a dialysis treatment, both must be primed with a sterile saline solution to remove air from the extracorporeal circuit. Once primed, the saline solution is recirculated through the blood tubing set and the dialyzer to produce a stabilized flow and remove additional trapped air from within the extracorporeal circuit. The priming and recirculating process also serves to clean the dialyzer and flush the dialyzer membrane of any debris or chemicals remaining from a prior use.

If a patient reuses the same dialyzer for subsequent dialysis treatments, that dialyzer must be cleaned with a disinfectant or sterilant solution. However, the sterilant itself must be cleaned from the dialyzer prior to each dialysis treatment. Such a cleaning procedure effectively takes place when the dialyzer undergoes the priming and recirculating process discussed above.

After completion of the prime and recirculation steps (i.e., when the blood tubing set is filled with saline), the arterial line of the blood tubing set is connected to the patient in the usual manner of dialysis systems. Blood is then drawn from the patient into the arterial line by a blood pump. The blood tends to replace the saline within the blood tubing set, and the saline is discarded down a waste drain until the blood tubing set is substantially filled with blood. The venous line is then connected to the patient to complete the extracorporeal circuit and allow the blood to travel through the arterial line, the dialyzer and back to the patient through the venous line.

At the conclusion of the dialysis treatment, but before the patient is completely disconnected from the dialysis machine, blood remaining in the blood tubing set must be returned to the patient. This is typically accomplished in one of two ways. One procedure requires clamping and disconnecting the arterial line from the patient and then attaching the arterial line to a saline source. The arterial clamp is then opened and the blood pump is started to draw saline into the arterial line and force the remaining blood through the arterial line, the dialyzer, and the venous line and back into the patient. When substantially all the blood has been returned to the patient, the venous line is clamped and the pump is stopped. The patient can then be disconnected from the dialysis machine.

Another procedure for returning the blood remaining within the blood tubing set to the patient entails using the same saline source that is used to prime the blood tubing set. The saline source is connected to the arterial reservoir of the blood tubing set and the saline is gravity fed into the arterial reservoir to force the blood in the arterial line back into the patient. Once the blood within the arterial line has been returned to the patient and the arterial reservoir has been filled with saline, the arterial line is clamped and the blood pump is activated to pump the saline through the dialyzer and the venous reservoir to force the remaining blood back into the patient through the venous line. Once substantially all the blood has been returned to the patient, the venous line is clamped and the patient is disconnected from the dialysis machine.

Although both procedures return substantially all the patient's blood, neither procedure returns 100% of the blood. Thus, the saline within the blood tubing set is contaminated with the patient's blood. The blood tubing set is thus usually discarded with the remaining contaminated saline left inside.

Due to the contaminated saline, the blood tubing set is necessarily classified as bio-hazardous medical waste which is relatively expensive to dispose of in comparison to normal refuse. Bio-hazardous medical waste cannot be discarded as normal trash, but rather must be sealed and removed by special contractors. Hospitals and dialysis clinics must typically pay a premium price for every pound of medical waste.

Since the used blood tubing set is typically filled with contaminated saline, this "water weight" significantly increases the disposal cost of the blood tubing set.

Additionally, if the dialyzer is to be reused, it must be detached from the blood tubing set before the set is discarded. This is typically accomplished by clamping the blood tubing set at the inlet and the outlet of the dialyzer so that the dialyzer can be detached without spilling the contaminated saline remaining within the blood tubing set. The dialyzer can then be reprocessed after the blood tubing set is discarded, but the dialyzer must be handled carefully due to the contaminated saline remaining within the blood compartment of the dialyzer.

Some clinics have attempted to recycle the blood tubing set together with the reusable dialyzers. However, reprocessing the dialyzer entails connecting the dialyzer to a different machine which can flush sterilant through the dialyzer. Thus, recycling the blood tubing set with the dialyzer requires extending the functionality of the dialyzer flushing machine to also flush the contaminated saline from the blood tubing sets. Two potentially serious problems may be associated with this recycling method. First, the dialyzer flushing machine is not adapted to handle the blood tubing set and thus the time and effort required to clean the blood tubing set on the machine is typically not cost-effective in relation to the cost of a new disposable blood tubing set. Secondly, and potentially more serious, the operator is required to handle the contaminated blood tubing set in an environment which the manufacturers of the "disposable" blood tubing set did not intend, thereby exposing the operator to very serious health risks.

These and other considerations have contributed to the evolution of the present invention which is summarized below.

SUMMARY OF THE INVENTION

One of the significant aspects of the present invention pertains to a method of disinfecting a contaminated blood tubing set while the blood tubing set remains attached to a dialysis machine following a dialysis procedure. Another significant aspect of the present invention relates to disinfecting a blood tubing set without requiring a dialysis machine operator to substantially handle the contaminated blood tubing set after the patient has been disconnected from the blood tubing set. A further significant aspect of the present invention relates to disinfecting a blood tubing set so that the blood tubing set may be discarded as refuse rather than bio-hazardous medical waste. A still further significant aspect of the present invention pertains to disinfecting a dialyzer in conjunction with a blood tubing set so that the dialyzer may be safely handled by the dialysis machine operator. A further aspect of the present invention pertains to expelling a majority of the fluid within a blood tubing set and a dialyzer to enhance the handling and the disposal cost of the blood tubing set and dialyzer.

In accordance with these and other aspects, the present invention may be generally summarized as a method of disinfecting a blood tubing set which has been contaminated with a patient's blood following a dialysis procedure. The blood tubing set is typically filled with saline at the conclusion of a dialysis treatment to return the patient's blood remaining within the blood tubing set and the attached dialyzer. Following disconnection from the patient, one end of the blood tubing set is preferably attached to a disinfection port on the dialysis machine while the opposite end of the blood tubing set is attached to a waste drain. The dialysis machine provides a supply of a disinfectant solution to the port and then pumps the solution through the blood tubing set and the dialyzer to flush the contaminated saline within the dialyzer down the waste drain. The disinfectant solution is preferably heated by a heater within the dialysis machine.

The method of the present invention also provides for the dialysis machine to pump other solutions through the blood tubing set, such as water, bleach (or other cleaning solutions), or even air. For instance, a water rinse may be provided to flush out the disinfectant solution after the disinfectant solution has flushed the contaminants from the blood tubing set. Additionally, air may be pumped through both the blood tubing set and the dialyzer to substantially remove the fluid from the blood tubing set and the dialyzer before they are detached from the dialysis machine.

The present invention also includes a dialysis machine capable of supplying the desired disinfectant solution to the blood tubing set. The dialysis machine preferably utilizes a number of hydraulic elements which are also utilized to create the dialysate used to cleanse the patient's blood during the dialysis treatment. These hydraulic elements include a water source and a heater for mixing and heating the disinfectant solution and for rinsing the disinfectant solution from the blood tubing set. The dialysis machine also includes a source of air which may be used to substantially purge the blood tubing set and the dialyzer of fluid.

The dialysis machine also preferably transfers the disinfectant solution to the blood tubing set from a disinfection port which is easily accessible to the dialysis machine operator. Additionally, the dialysis machine preferably includes a waste handling port so that the operator may conveniently attach the blood tubing set between the disinfection port and the waste handling port (after detaching the blood tubing set from the patient) with minimal risk of being exposed to the contaminated fluid within the blood tubing set.

A more complete appreciation of the present invention and its scope may be obtained from the accompanying drawings, which are briefly summarized below, from the following detailed descriptions of presently preferred embodiments of the invention, and from the appended claims.

DETAILED DESCRIPTION

Figure 1:
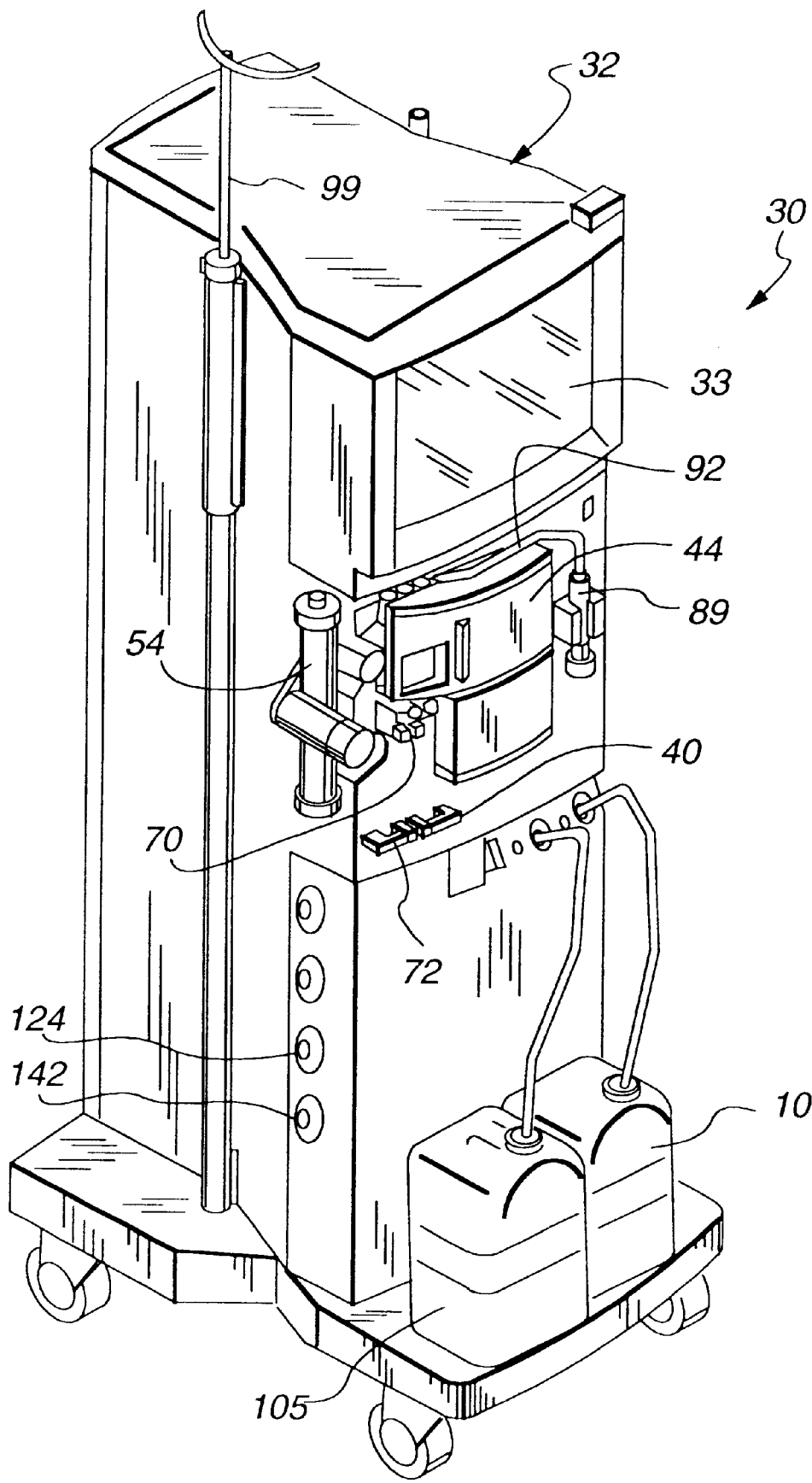
FIG. 1 is a perspective view of a dialysis machine which incorporates the present invention.
Figure 2:
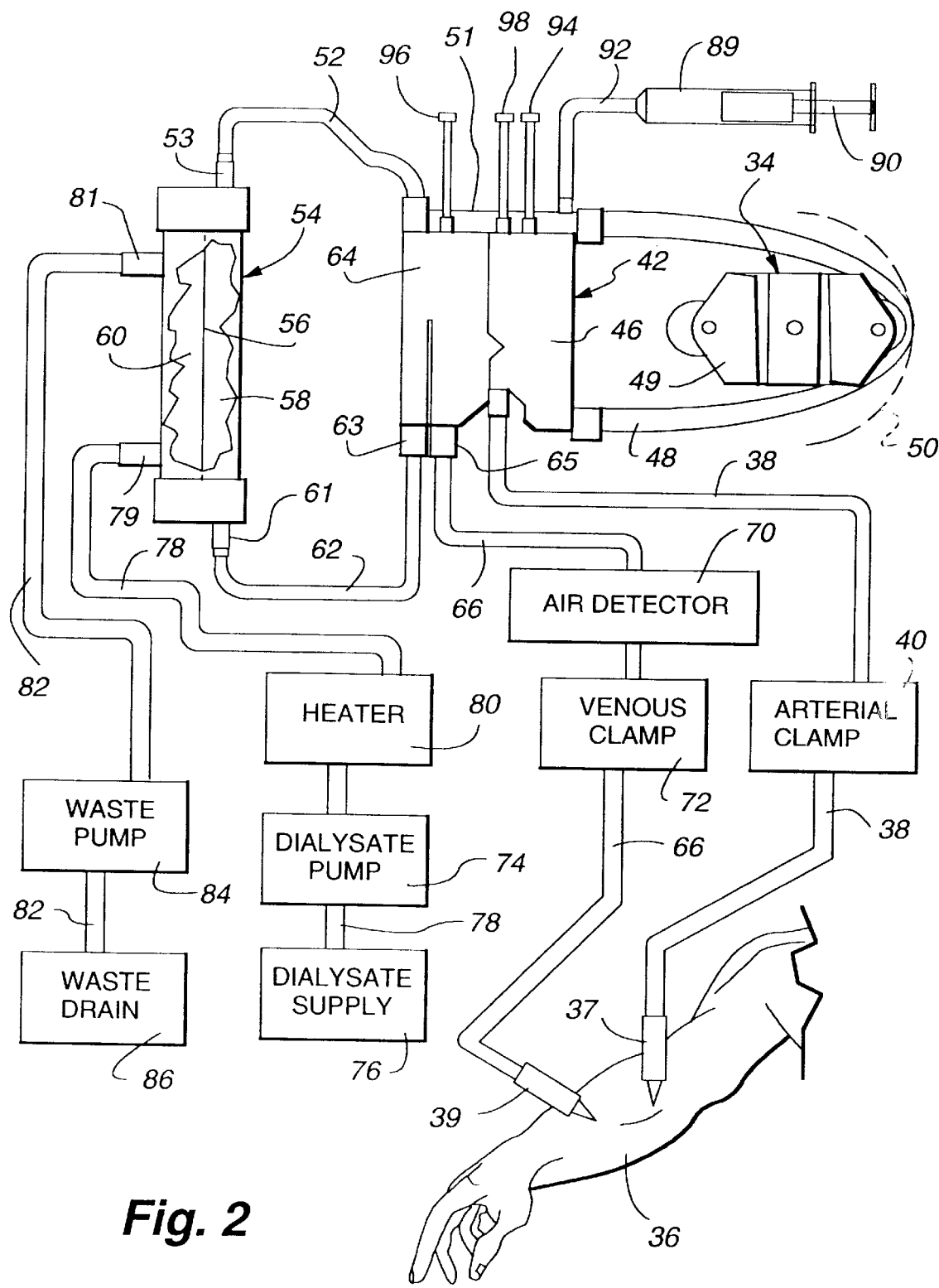
FIG. 2 is a generalized view illustrating a dialyzer, an extracorporeal blood flow path from a patient through the dialyzer, and a dialysate flow path through the dialyzer, as are present during treatment of a patient with the dialysis machine shown in FIG. 1.

An example of a dialysis machine with which the present invention may be advantageously employed is shown at 30 in FIG. 1. The dialysis machine 30 includes an enclosure 32 to which are attached, or within which are housed, those functional devices and components of the dialysis machine 30 which are generally illustrated in FIG. 2. The enclosure 30 also includes a conventional input/output ("I/O") device for controlling the machine 30, such as a touch-screen monitor 33 as shown in FIG. 1.

The dialysis machine 30 includes at least one blood pump 34 which controls the flow of blood from a patient 36. An arterial line or tubing 38 is connected through an arterial clamp 40 to a blood handling cartridge 42. The blood handling cartridge 42 is normally retained behind a door 44 (FIG. 1) of the machine 30 when used, thus the blood handling cartridge 42 is not shown in FIG. 1. The blood pump 34 also is located behind the door 44 adjacent to the cartridge 42. The blood pump 34 in dialysis machines is typically a peristaltic pump.

The patient 36 is connected to an extracorporeal flow circuit by an arterial connector 37 and a venous connector 39. Blood from the patient 36 flows through the extracorporeal circuit when the arterial clamp 40 is open and the blood pump 34 draws blood from the patient 36. The blood passes through the arterial line 38 and into an arterial reservoir 46 of the cartridge 42. The blood pump 34 draws blood from the arterial reservoir 46 through a pump header 48 which is squeezed or pinched by a rotating rotor 49 against a stationary raceway 50, in the typical manner of peristaltic pumps. The blood within the pump header 48 which is rotationally in front of the rotor 49 is propelled through the pump header 48 and into a manifold 51 of the cartridge 42. A tubing 52 conducts the blood from the manifold 51 of the cartridge 42 into a blood inlet 53 of a conventional dialyzer 54. A microporous membrane or other type of dialysis medium 56 divides the interior of the dialyzer 54 into a blood chamber 58 and a dialysate chamber 60.

As the patient's blood passes through the dialyzer 54, the waste products within the blood pass through the medium 56 where they mix with the dialysate in the chamber 60. The cleansed blood exits the dialyzer 54 through a blood outlet 61 and is then transferred through a tubing 62 to an inlet 63 of a venous reservoir 64 of the cartridge 42. Any air which might have been unintentionally introduced into the blood is collected and removed while the blood is in the venous reservoir 64. Blood exits the venous reservoir 64 through an outlet 65 and is removed from the cartridge 42 through a venous tubing or line 66.

After leaving the venous reservoir 64, the blood flows through the venous line 66 to an air detector 70. The air detector 70 derives signals related to the quantity of air, if any, remaining in the venous line 66. If an excessive or dangerous amount of air is present, a venous line clamp 72 will immediately close and the blood pump 34 will stop to terminate the flow of blood through the venous line 66 before the detected air reaches the patient 36.

The enclosure 32 of the dialysis machine 30 also encloses the various elements of a dialysate flow path, shown in abbreviated form in FIG. 2. The elements of the dialysate flow path include a number of different valves (most of which are not shown) and a dialysate pump 74 which draws dialysate from a container 76 or from an internal supply of dialysate which the dialysis machine 30 has prepared from appropriate chemicals and a supply of purified water.

The dialysate pump 74 draws the dialysate from the supply 76 and delivers the dialysate through a dialysate supply tubing or line 78 to an inlet 79 of the dialysate chamber 60 of the dialyzer 54. The dialysate flows past the medium 56 where it absorbs the waste products from the blood in the blood chamber 58. Any beneficial components within the dialysate which are desired to be transferred to the blood pass through the medium 56 and enter the blood in the blood chamber 58. The dialysate containing the waste products then exits the dialysate chamber 60 through an outlet 81 and is removed from the dialyzer 54 through a dialysate waste tubing or line 82 by operation of a drain pump 84.

Prior to reaching the dialyzer 54, a heater 80 heats the dialysate to normal human body temperature. Because the dialysate and the blood will readily transfer heat across the medium 56 within the dialyzer 54, it is important that the dialysate be at body temperature to prevent excessive heat transfer to or from the patient.

The dialysate removed from the dialyzer 54 is delivered through the waste tubing 82 to a waste basin or drain 86. The waste drain 86 may be a separate container which receives the used dialysate and accumulated waste products, or it may simply be a drain to a public sewer. The various valves and pumps which control the dialysate flow path are referred to generally as the dialysate hydraulics.

Because the blood in the extracorporeal flow path is prone to clot, it is typical to inject an anticoagulant such as heparin into the extracorporeal flow path. The typical approach to injecting the anticoagulant is to slowly deliver it from a syringe 89. A plunger 90 of the syringe is slowly and controllably displaced into the syringe 89 by a linear driver mechanism (not shown), which is typically referred to as the anticoagulant pump. Anticoagulant from the syringe 89 is introduced into the manifold 51 of the cartridge 42 through a tubing 92 connected to the syringe as shown in FIG. 2. The anticoagulant pump is controlled to deliver the desired amount of anticoagulant during the dialysis treatment by the degree to which the anticoagulant pump moves the plunger 90 into the syringe 89 over a given time period.

Tubings 94 and 96 are respectively connected to the arterial reservoir 46 and venous reservoir 64 of the cartridge 42 as shown in FIG. 2. Clamps or caps (not shown) are connected to the ends of the tubings 94 and 96 to selectively vent accumulated air from the reservoirs 46 and 64. A saline tubing 98 is also connected to the arterial reservoir 46 so that saline may be directly administered to the patient during treatment in case of low blood pressure. A pole 99 for supporting a conventional saline bag is attached to a side of the enclosure 32, as shown in FIG. 1. Additionally, medicines or other additives may be introduced into the blood through the access tubing 94 during treatment.

The reservoirs 46 and 64 and the manifold 51 of the blood handling cartridge 42, together with the tubes 38, 48, 52, 62 and 66, are collectively referred to as a blood tubing set ("BTS"). The BTS is disposable and is typically thrown away after each dialysis treatment. Similarly, the dialyzer 54 is termed a disposable product, although it is not uncommon for a dialyzer to be reused with a single patient. A dialyzer will typically be reused by a patient who regularly visits the same clinic for dialysis treatments. Following each treatment, the dialyzer is cleaned with a sterilant and is then stored until the patient's next visit to the clinic. The dialyzer must then be thoroughly cleaned before use to ensure that the sterilant is not transferred to the patient's bloodstream during the next dialysis treatment.

Before each treatment, the disposable BTS and the dialyzer 54 (regardless of whether the dialyzer is new or "used") must be attached to a dialysis machine 30 and prepared for a patient's use by an operator. While the disposable BTS is sterile and thus does not need to be cleaned, the BTS and the dialyzer 54 must be primed with a sterile saline solution to remove the air from the extracorporeal circuit. In addition to flushing the dialyzer 54 with saline solution during priming, the saline solution must be recirculated through the dialyzer for a predetermined period of time to ensure that substantially all of the sterilant or other chemical debris within the dialyzer has been removed. This recirculation process also establishes a stable flow within the extracorporeal circuit and ensures that any remaining air within the circuit has been removed before the patient is connected to the machine 30. Once the priming and recirculating process is completed and the circuit is filled with saline, the arterial connector 37 is attached to the patient and the patient's blood is drawn through the circuit. The venous line 66 is connected to the waste drain 86 to dispose of the used saline solution and, at the point the patient's blood has displaced all the saline within the circuit, the venous connector 39 is connected to the patient, as shown in FIG. 2.

Figure 3:
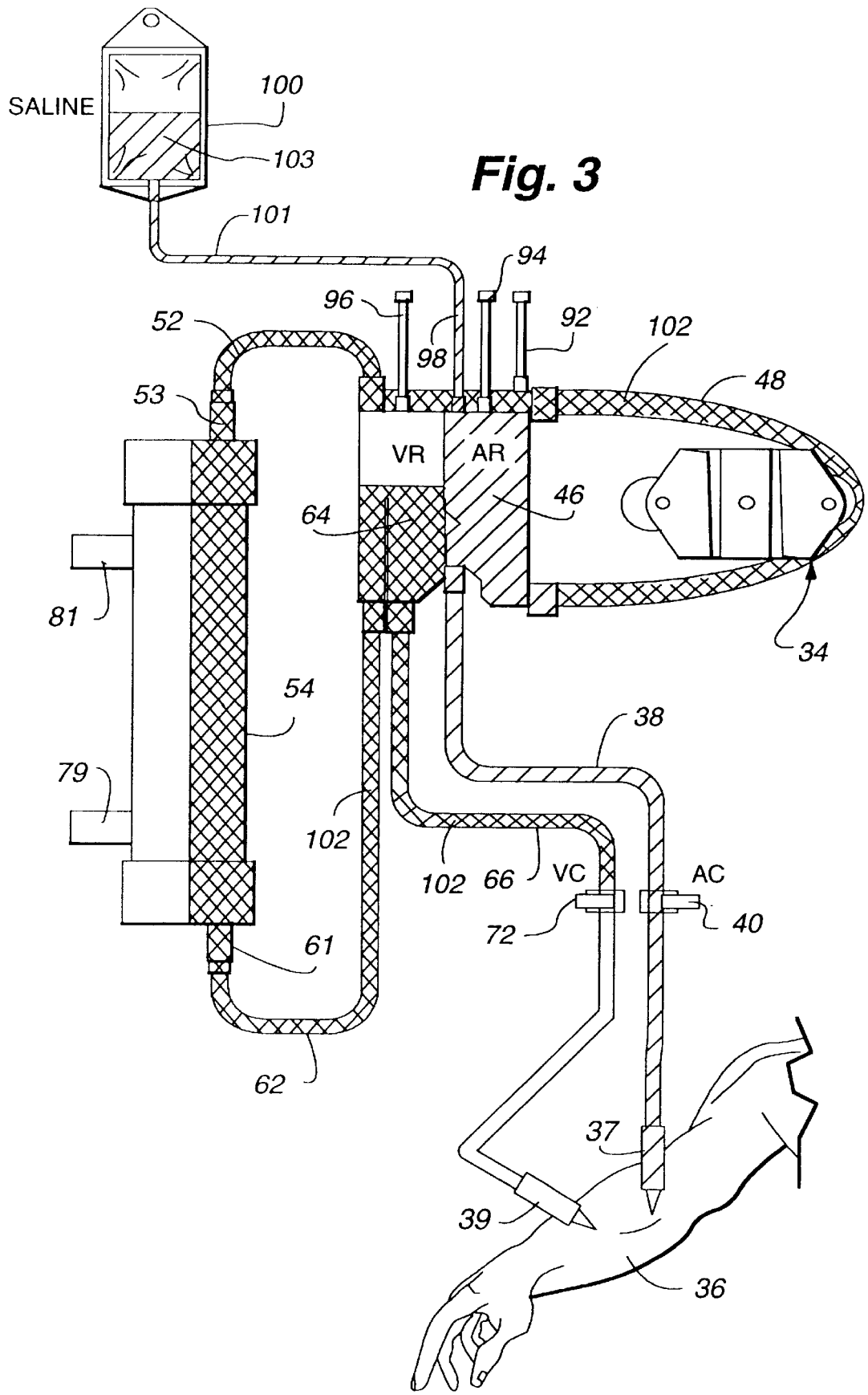
FIG. 3 is a generalized view of a dialyzer connected to a blood tubing set which together define the extracorporeal flow path shown in FIG. 2, and illustrating a saline source connected to the blood tubing set at the conclusion of a dialysis treatment forcing blood remaining within the blood tubing set to return to the patient.

The same saline source used to prime the BTS is also preferably used during the dialysis treatment to mix saline with the patient's blood when the patient experiences low blood pressure. This saline source typically comprises a saline bag 100 (FIGS. 3 and 4) which is attached to the pole 99 (FIG. 1) on the dialysis machine 30. A tube 101 connects the saline bag 100 to the saline tubing 98 that leads to the arterial reservoir 46.

Figure 4:
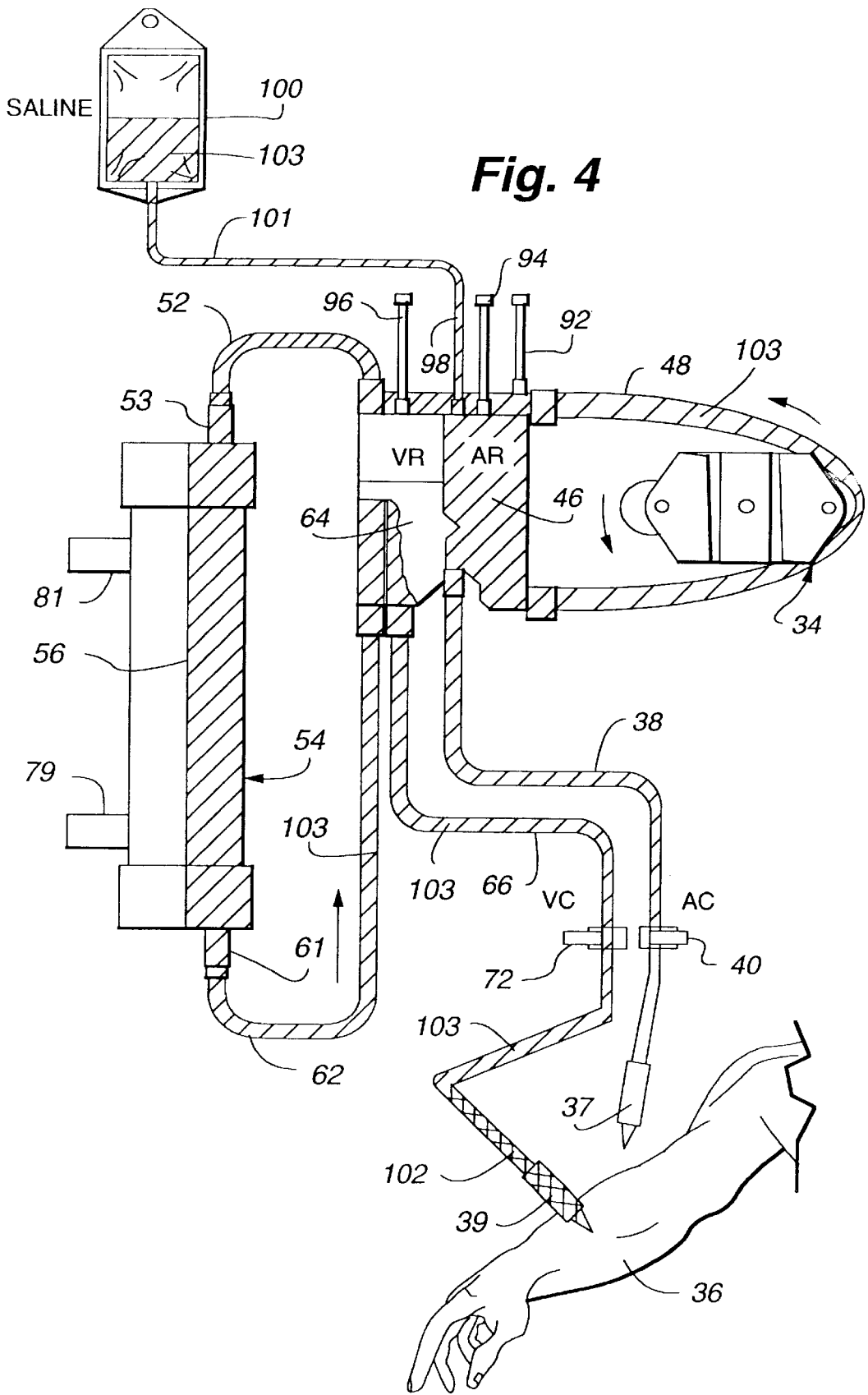
FIG. 4 is a generalized view similar to FIG. 3, illustrating the saline source working with a blood pump shown in FIG. 2 to force the remainder of the blood within the extracorporeal flow path to return to the patient.

The saline bag 100 may also be used at the conclusion of the dialysis treatment to return the blood 102 remaining within the BTS to the patient. When used in this manner, a clamp on the tube 98 or the saline line 101 may be opened after the blood pump 34 is halted at the conclusion of the dialysis treatment. Gravity will then operate to draw saline 103 from the bag 100 into the arterial reservoir 46 (FIG. 3) and force the blood remaining within the arterial reservoir 46 and the arterial line 38 back into the patient 36. The arterial clamp 40 is then closed so that the arterial connector 37 may be removed from the patient (FIG. 4). Next, the blood pump 34 is started to draw saline 103 from the arterial reservoir 46 and the bag 100 through the dialyzer 54 and the venous reservoir 64. Pumping saline 103 from the bag 100 in this manner effectively "chases" the remaining blood 102 through the extracorporeal circuit so that the blood is forced through the venous line 66 and back into the patient 36. Once the saline 103 has displaced substantially all the blood 102 from the BTS, the venous clamp 72 is closed so that the venous connector 39 may be detached from the patient.

Although using the saline bag 100 is the preferred method of "chasing" the patient's blood out of the BTS, an alternative method of attaching a separate saline source to the arterial connector 37 and operating the pump 34 may also be used. All of the blood remaining within the BTS would then be "chased" around the entire extracorporeal circuit before being forced back into the patient through the venous line 66. However, this alternative method is not preferred because it requires the dialysis machine operator to physically connect the contaminated arterial connector 37 to an additional saline source.

Once the patient 36 is detached from the arterial and venous connectors 37 and 39, respectively, the dialysis machine 30 may be commanded to clean and disinfect the BTS before the BTS is detached from the machine. While the dialysate hydraulics and the BTS normally comprise completely separate flow paths (separated by the membrane 56 within the dialyzer 54 during the dialysis treatment), the dialysate hydraulics may be connected directly to the BTS for the limited purpose of cleaning and disinfecting the BTS before it is discarded. However, unlike the BTS which is discarded after each use, the dialysate hydraulics are reused and are typically cleaned and disinfected only once at the beginning of each day, and thus it is important to prevent the BTS from contaminating the dialysate hydraulics. Details regarding a technique for automatically cleaning and disinfecting the dialysate hydraulics may be found in the above-referenced U.S. patent application for Technique for Automatically Preparing a Dialysis Machine at a Predetermined Date and Time, the disclosure of which was previously incorporated by reference.

Figure 5:
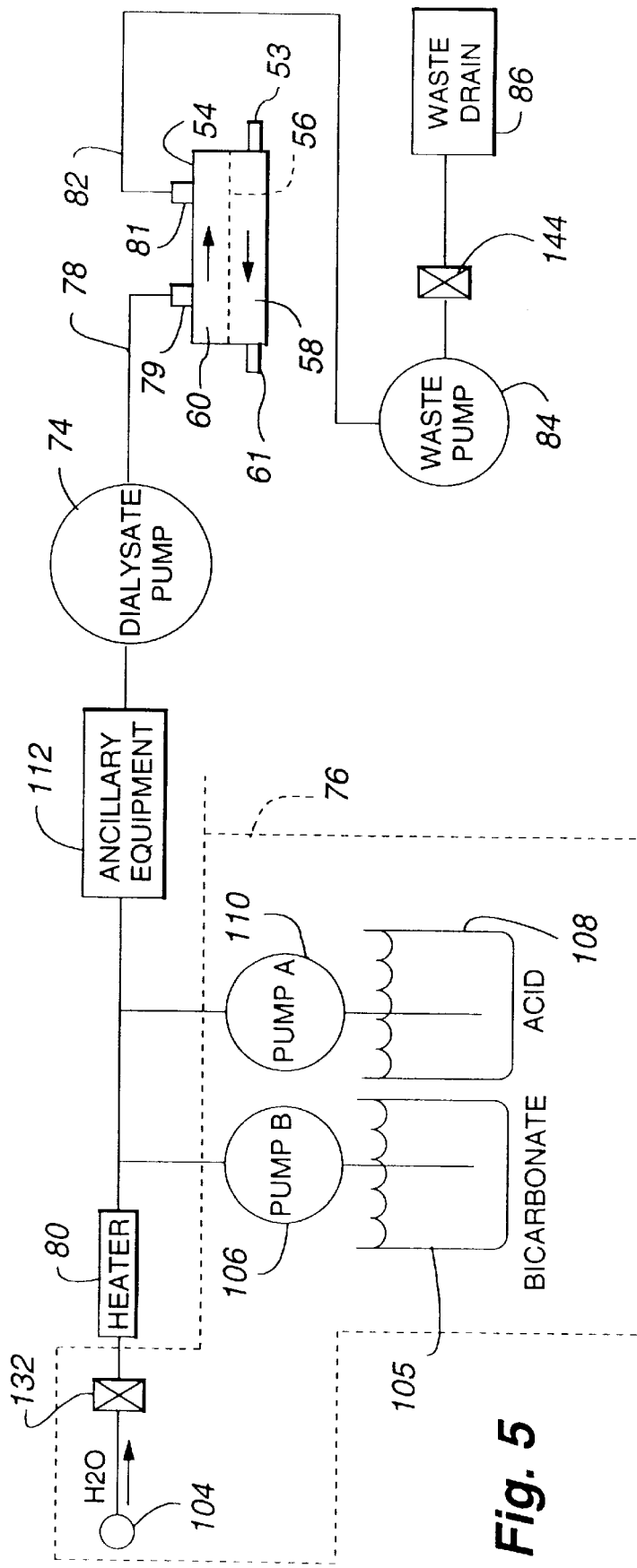
FIG. 5 is an expanded view of the dialysate flow path shown in FIG. 2 (including the dialyzer), where the extracorporeal blood flow path has been omitted for clarity.
Figure 6:
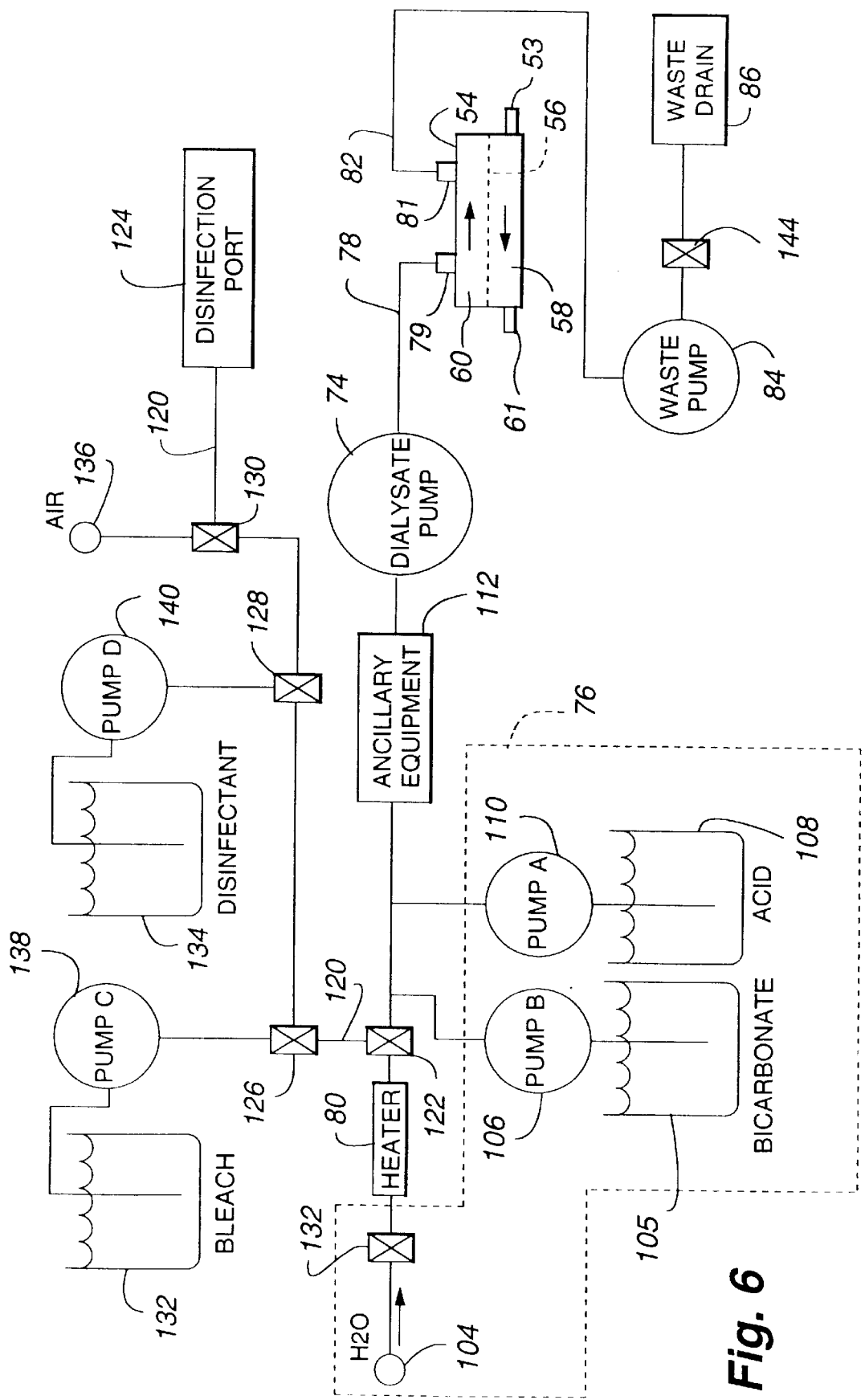
FIG. 6 is an expanded view of the dialysate flow path similar to FIG. 5, illustrating additional hydraulic components including a disinfection port of the present invention for disinfecting the blood tubing set shown in FIG. 2.

The dialysate hydraulics, which were shown in abbreviated fashion in FIG. 2, are shown in greater detail in FIGS. 5 and 6, although many components of the dialysis hydraulics have been omitted for clarity. When the dialysis machine 30 creates its own supply of dialysate, as opposed to using a previously prepared supply as shown in FIG. 1, the dialysate supply 76 preferably takes the simplified form shown in FIG. 5. The dialysate hydraulics creates the dialysate by mixing a flow of purified water from a source 104 with chemicals which typically include bicarbonate and acid. Bicarbonate is pumped from a source 105 by a pump labeled at 106 as "Pump B." Similarly, acid is pumped from a source 108 by a pump labelled at 110 as "Pump A." Additionally, the water is preferably heated by the heater 80 before it is mixed with the bicarbonate and acid within the dialysate line 78.

A number of various filters, sensors and other ancillary devices are generally shown at 112. A filter is typically necessary to remove any impurities from the dialysate before it enters the dialyzers. Additionally, the temperature, conductivity and pH level of the dialysate is sensed at 112. The sensors then control the heater 80 and the pumps 106 and 110 to maintain the temperature and composition of the dialysate within prescribed limits. Other ancillary equipment that may be generally represented at 112 includes bubble traps and degassing valves to ensure that no air bubbles are sent through the dialysate line 78 to the dialyzer 54.

During the dialysis procedure, the dialysate pump 74 pumps the mixed dialysate through the inlet 79 and into the dialysate chamber 60 of the dialyzer 54. The dialysate within the chamber 60 cleanses the patient's blood across the membrane or medium 56 as the BTS (not shown in FIG. 5) delivers the blood through the blood chamber 58 (between the inlet 53 and the outlet 61) of the dialyzer 54. The dialysate waste pump 84 then disposes of the used dialysate by pumping it from the dialyzer outlet 81 to the waste drain 86 through the waste line 82.

Thus, while the dialysate hydraulics are primarily responsible for the preparation of the dialysate, they may also be beneficially used to clean and disinfect the BTS. In general, once the dialysis treatment is complete and the BTS is filled with contaminated saline, the arterial line 38 may be connected to the dialysate hydraulics at a point separate from the dialysate line 78. The dialysate hydraulics may then be commanded to produce a supply of a cleaner or disinfectant to be pumped to the BTS by the blood pump 34. The cleaning and disinfectant solution may then be flushed through the BTS or, time permitting, it may be allowed to dwell within the BTS for a predetermined time. However, because the dialysis machine can not be prepared for another patient until the BTS is cleaned and removed from the machine, the cleaning/disinfecting solution is preferably flushed through the BTS in a relatively short time period. The dialysate hydraulics may optionally supply air to the BTS after it has been flushed with the disinfectant solution so that the blood pump 34 may pump the air through the BTS to substantially remove the solution from the BTS and the blood chamber 58 of the dialyzer 54. Upon the conclusion of the disinfection procedure, the BTS may be removed from the machine without risk of exposing the operator to the patient's blood. The BTS can then be disposed of as normal refuse instead of bio-hazardous medical waste. Alternatively, the dialysis hydraulics may simply use air to force the contaminated fluid from the BTS and the blood compartment of the dialyzer to reduce their weight without disinfecting the BTS.

The technique of the present invention requires the presence of additional hydraulic components not otherwise required by the dialysis machine 30 to produce and pump the dialysate through the dialyzer 54 during a dialysis treatment. Due to the length of time required to clean and disinfect the dialysate hydraulics, it is preferred that the dialysate line 78 not be utilized in the preparation of the solution for disinfecting the BTS. Rather, a separate disinfection line 120 branches from the dialysate line 78 at a control valve 122. The disinfection line connects with a disinfection port 124 protruding from the enclosure 32 of the dialysis machine 30. As discussed in greater detail below, the disinfection port 124 effectively connects one end of the BTS to the disinfection line 120 to flush the contaminated saline within the BTS down the waste drain 86 (FIG. 7).

The disinfectant line 120 preferably includes three separate control valves 126, 128 and 130 connected in series, as shown in FIG. 6. The valves 126, 128 and 130 are each respectively connected to a source of cleaning solution or bleach 132, a disinfectant source 134 and a source of air 136. Pumps 138 and 140 are preferably used to supply the bleach 132 and the disinfectant 134 to the valves 126 and 128, respectively. Under the control of a microprocessor (not shown), the control valves 122, 126, 128 and 130 may be operated to create any desired cleaning and/or disinfection mixture within the disinfection line 120. The mixture is preferably heated by the inclusion of water from the source 104 which is heated by the heater 80. A dialysis machine operator may choose the type of cleaning/disinfecting mixture desired from the I/O device 33 (FIG. 1). For example, if a heated disinfectant is desired, the operator would make the proper selection from the I/O device 33 and the microprocessor would operate the heater 80 and "Pump D" (140) to prepare the heated water and the disinfectant. The microprocessor would then open the valves 122 and 128 to mix the hot water with the disinfectant and allow the mixture to be pumped from the disinfection port 124.

Figure 7:
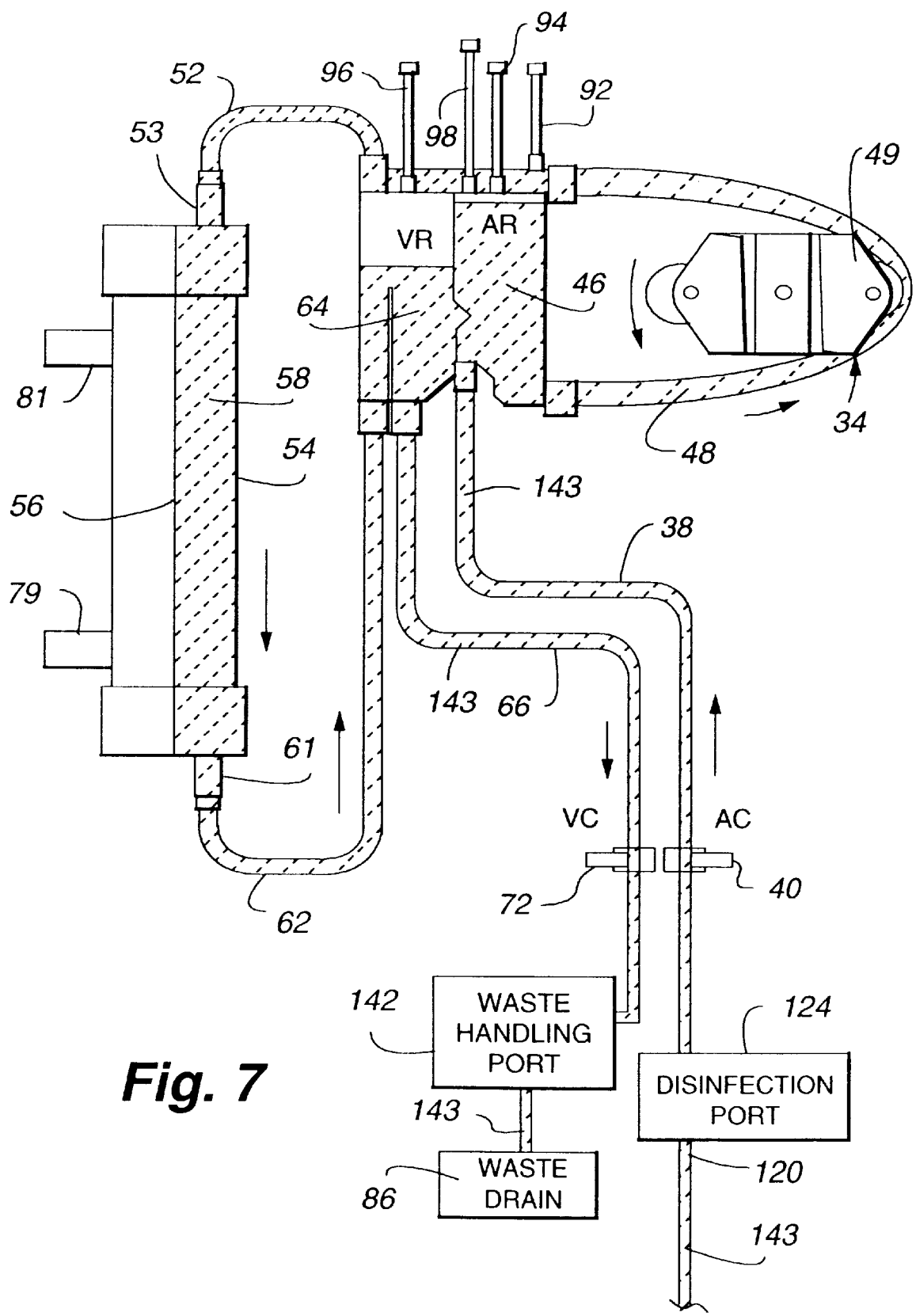
FIG. 7 is a generalized view similar to FIG. 3, illustrating the disinfection port shown in FIG. 6 connected to the extracorporeal flow path shown in FIG. 2 for disinfecting the blood tubing set.

The connection of the BTS to the disinfection port 124 is illustrated in FIG. 7. The clamped arterial line 38 is preferably attached to the port 124, while the clamped venous line 66 is preferably attached to the waste drain 86. Alternatively, the venous line 66 may be attached to a waste handling port 142 (FIGS. 1 and 7) which, in turn, is connected to the waste drain 86. Details of such a waste handling port 142 for use on a dialysis machine may be found in U.S. Pat. No. 5,041,215, entitled Dialysis Unit Priming and assigned to the assignee hereof, the disclosure of which is incorporated herein by this reference.

Once the arterial and venous lines 38 and 66 are connected as shown in FIG. 7, the operator may command the dialysis machine 30 to begin disinfecting the BTS. Depending on the type of disinfection procedure requested, the microprocessor will open one or more of the valves 122, 126, 128 and 130, and operate the pumps 138 and 140, to prepare a disinfectant solution 143 within line 120. The microprocessor will then open the arterial and venous clamps 40 and 72 and start the blood pump 34 to draw the disinfectant solution 143 through the port 124 and into the arterial line 38. The blood pump 34 then continues to flush the disinfectant solution 143 through the BTS and the blood chamber 58 of the dialyzer 54 until all the contaminated fluid within the dialyzer and BTS has been forced through the venous line 66 and the waste handling port 142. The BTS may then be detached from the dialysis machine 30 and the dialyzer 54 and discarded.

If time permits, the BTS and dialyzer 54 may be flushed more than one time with different combinations of solutions. For example (and not by way of limitation), a heated cleaning solution consisting of water from the source 104 (heated by the heater 80) mixed with a bleach or other commercially available sterilant from the source 132 may initially be supplied to the disinfection port 124. Following a predetermined time, while the blood pump 34 continues to operate, the valves 122 and 126 may be closed, and the valve 128 may be opened so that disinfectant from the source 134 is drawn through the port 124. Lastly, the valve 128 may be closed and the valve 122 opened again to provide a final water rinse for the BTS and the dialyzer 54.

As an optional step (not shown), once the contaminated saline solution has been expelled from the BTS and dialyzer, the valve 130 may be opened to allow the blood pump 34 to pump air from the source 136 through the BTS and dialyzer 54 to force a majority of the disinfectant solution 143 out of the BTS and the blood chamber 58 of the dialyzer and into the waste handling port 142. Air may also be pumped through the dialysate line 78 to flush remaining dialysate from the dialysate chamber 60 of the dialyzer 54. In this manner, the substantially dry BTS may be more easily handled and discarded than a BTS which is still filled with the disinfectant solution.

The BTS preferably remains attached to the dialyzer 54 during the cleaning/disinfection procedure. While the tubes 52 and 62 of the BTS could be connected together to bypass the dialyzer 54 during the disinfection procedure, this approach is not recommended for several reasons. First, an operator runs the risk of contacting the contaminated saline solution while disconnecting the dialyzer 54 from the BTS and connecting the tubes 52 and 62. Additionally, flushing the contaminated saline from the blood chamber 58 of the dialyzer 54 makes the dialyzer 54 safer to handle. As noted above, dialyzers are frequently reused by a single patient and thus must be sterilized between uses. While the disinfection procedure of the present invention may be insufficient to completely sterilize the dialyzer for later use, the initial disinfection which it receives during the disinfection of the BTS reduces the health risks to dialysis machine operators who must later sterilize and recycle the dialyzer. Additionally, if the dialyzer is to be discarded after the dialysis treatment (i.e., it is disposable), the disinfection procedure of the present invention may be sufficient to disinfect the dialyzer in addition to the BTS so that both may be discarded as refuse rather than bio-hazardous waste.

The valves 122, 126, 128 and 130 may operate in a known manner to prevent the contaminated solution within the BTS from being drawn through the disinfection port 124 and into the dialysate line 78. Additionally, a valve 144 (FIGS. 5 and 6) is preferably placed within the dialysate waste line 82 to prevent contaminants from being drawn into the dialyzer 54 from the waste drain 86. Thus, the BTS may be disinfected without fear of contaminating the dialysate line 78. This is a significant consideration in light of the fact that the dialysis machine 30 may be used to perform a number of dialysis procedures in a day, while the dialysate hydraulics are typically only cleaned and disinfected at the start of the day.

Additionally, while the sources 132 and 134 and the pumps 138 and 140 are preferably separate from similar sources and pumps used within the dialysate hydraulics to reduce the potential for contaminating the dialysate hydraulics, one skilled in the art may utilize the existing components of the dialysate hydraulics shown in FIG. 5 to attain the functionality of the separate components shown in FIG. 6.

The ability to quickly connect the arterial and venous lines 38 and 66 to the disinfection port 124 and the waste handling port 142, respectively, is a significant advantage due to the typical desire of dialysis clinics to treat as many patients as possible in a given day. The BTS and the dialyzer may thus be disinfected in a relatively short time period. Indeed, if there is insufficient time to pump the chemical disinfectant through the BTS, air from the source 136 may be used to quickly push the majority of the contaminated fluid from both the dialyzer and the BTS. Thus, while the BTS still need to be disposed of as bio-hazardous waste, it will be easier and safer for an operator to handle and the clinic will not have to pay for the extra weight of the contaminated solution.

Of course, the main benefit of the present invention will only be achieved if the BTS can be sufficiently cleaned or disinfected to prevent its being classified as bio-hazardous waste. Thus, for the cost of the chemicals used in the disinfection procedure and the time required to complete the procedure (during which the dialysis machine can not be used with a patient), a hospital or dialysis clinic will reap several rewards. First, operators who must handle the BTS after the procedure will no longer be at risk of contacting the contaminated solution that remains within the BTS at the conclusion of the dialysis treatment. Secondly, the BTS may now be easily discarded as refuse resulting in a great monetary savings to the dialysis clinic.

Additionally, while the primary benefit of the present invention relates to disinfecting the BTS, a further significant benefit is achieved by simultaneously disinfecting the dialyzer. If the dialyzer is to be further sterilized for later reuse, or if the dialyzer is to be discarded after the treatment, the initial disinfection which it receives in conjunction with the BTS will significantly reduce the risks associated with handling the dialyzer after the treatment.

A presently preferred embodiment of the present invention and many of its improvements have been described with a degree of particularity. This description is a preferred example of implementing the invention, and is not necessarily intended to limit the scope of the invention. The scope of the invention is defined by the following claims.

The invention claimed is:

1. A dialysis machine usable for both dialyzing blood of a patient in a dialysis treatment and disinfecting a contaminated blood tubing set following use of the blood tubing set in the dialysis treatment, the blood tubing set having an arterial line and a venous line and adapted to be connected to a blood chamber of a dialyzer used during the dialysis treatment, said dialysis machine further including a dialysate supplying system for supplying dialysate solution through a dialysate flow path to a dialysate chamber of the dialyzer during the dialysis treatment, said dialysis machine further comprising:

a waste drain adapted to be connected to one of the arterial line and the venous line of the blood tubing set following the dialysis treatment;

a disinfectant supplying system for preparing a disinfectant solution and supplying the disinfectant solution in a disinfectant flow path which is separate and isolated from the dialysate flow path, the disinfectant solution not being suitable for use as the dialysate solution;

a disinfection port connected in the disinfectant flow path and adapted to be connected to the other one of the arterial and venous lines of the blood tubing set following the dialysis treatment, said disinfection port adapted to conduct the disinfectant solution from the disinfectant flow path to said other one of the arterial and venous lines; and a pump to pump the disinfectant solution from the disinfection port through the arterial and venous lines of the blood tubing set and to the waste drain; and wherein:
  the separate and isolated disinfectant flow path preserves the dialysate solution and the dialysate flow path in condition for immediate resumption of another dialysis treatment using a new blood tubing set after disinfecting the previous blood tubing set and without cleaning and disinfecting the dialysate flow path before connecting the new blood tubing set into the dialysate flow path.

2. A dialysis machine as defined in claim 1 wherein the waste drain is adapted to be connected to the venous line and the disinfection port is adapted to be connected to the arterial line.

3. A dialysis machine as defined in claim 1, wherein the disinfectant supplying system further comprises:

a source of disinfectant solution; and a disinfection source pump to pump the disinfectant solution from the disinfectant solution source into the disinfectant flow path to the disinfection port.

4. A dialysis machine as defined in claim 3, further comprising:

a heater to heat the disinfectant solution prior to delivery from the disinfection port.

5. A dialysis machine as defined in claim 1 wherein the pump which pumps the disinfectant solution through the blood tubing set during disinfection of the blood tubing set also pumps blood through the blood tubing set during the dialysis treatment, the cleaning solution not being suitable for use as the dialysate solution.

6. A dialysis machine as defined in claim 1, wherein the disinfectant supplying system also prepares a cleaning solution for cleaning the blood tubing set and supplies the cleaning solution in the disinfectant flow path.

7. A dialysis machine as defined in claim 6, wherein the disinfectant supplying system further comprises:

a source of cleaning solution; and a cleaning solution source pump to pump the cleaning solution from the cleaning solution source into the disinfectant flow path to the disinfection port.

8. A dialysis machine as defined in claim 6 wherein the pump which pumps the cleaning solution through the blood tubing set during cleaning of the blood tubing set also pumps blood through the blood tubing set during the dialysis treatment.

9. A dialysis machine as defined in claim 7, further comprising:

a heater to heat the cleaning solution prior to delivery from the disinfection port.

10. A dialysis machine as defined in claim 6, wherein the disinfectant supplying system is selectively controllable to supply one of either the disinfectant solution or the cleaning solution through the disinfectant flow path.

11. A dialysis machine as defined in claim 6, wherein the disinfectant supplying system also prepares a gaseous fluid for removing the disinfectant solution and the cleaning solution from within the blood tubing set and supplies the gaseous fluid in the disinfectant flow path.

12. A dialysis machine as defined in claim 11, wherein the disinfectant supplying system further comprises:

a source of gaseous fluid; and a pump to pump the gaseous fluid from the gaseous fluid source into the dialysate flow path to the disinfection port.

13. A dialysis machine as defined in claim 11, wherein the source of gaseous fluid comprises:

an air source; and the disinfectant supplying system further comprises:

a valve adapted to supply air from the air source to the disinfection port.

14. A dialysis machine as defined in claim 12 wherein the gaseous fluid comprises air.

15. A dialysis machine as defined in claim 1, wherein the disinfectant supplying system also prepares a gaseous fluid for removing the disinfectant solution from within the blood tubing set and supplies the gaseous fluid in the disinfectant flow path.

16. A dialysis machine as defined in claim 15 wherein the pump which pumps the gaseous fluid through the blood tubing set also pumps blood through the blood tubing set during the dialysis treatment.

17. A dialysis machine as defined in claim 1 wherein:

input fluid is supplied to both the dialysate preparing system and the disinfectant supplying system for use in making up the dialysate solution and the disinfectant solution;

the dialysate solution is prepared in the dialysate flow path downstream of a location where the input fluid is supplied to the dialysate preparing system; and the disinfectant solution is created in the disinfectant flow path downstream of a location where the input fluid is supplied to the disinfectant supplying system.

18. A dialysis machine as defined in claim 17 wherein the input fluid is water.

19. A dialysis machine as defined in claim 1, wherein the dialyzer remains connected to the blood tubing set during disinfection, and the disinfectant solution flows through the blood chamber of the dialyzer during disinfection.

20. A dialysis machine as defined in claim 18, further comprising:

a water source; and a valve adapted to conduct water from the water source into the disinfectant flow path and into the dialysate flow path.

21. A dialysis machine as defined in claim 20, further comprising:

a heater to heat the water from the water source prior to conducting the water into the dialysate and disinfectant flow paths.

* * * * *